United States Patent
Chiba et al.

(10) Patent No.: US 8,309,510 B2
(45) Date of Patent: Nov. 13, 2012

(54) SURFACTANT COMPOSITION

(75) Inventors: Keisuke Chiba, Wakayama (JP);
Toshihiro Tanaka, Wakayama (JP);
Takeshi Tomifuji, Wakayama (JP)

(73) Assignee: Kao Corporation, Tokyo (JP)

( * ) Notice: Subject to any disclaimer, the term of this patent is extended or adjusted under 35 U.S.C. 154(b) by 420 days.

(21) Appl. No.: 12/601,214

(22) PCT Filed: Jul. 9, 2008

(86) PCT No.: PCT/JP2008/062774
§ 371 (c)(1),
(2), (4) Date: Dec. 17, 2009

(87) PCT Pub. No.: WO2009/008542
PCT Pub. Date: Jan. 15, 2009

(65) Prior Publication Data
US 2010/0160206 A1 Jun. 24, 2010

(30) Foreign Application Priority Data
Jul. 9, 2007 (JP) .................................. 2007-179989

(51) Int. Cl.
*C11D 1/80* (2006.01)
(52) U.S. Cl. ..................................... 510/467; 252/182.3
(58) Field of Classification Search .................. 510/467; 252/182.3
See application file for complete search history.

(56) References Cited

U.S. PATENT DOCUMENTS

| | | | |
|---|---|---|---|
| 2,560,333 A * | 7/1951 | Keiser et al. | 516/183 |
| 3,843,706 A * | 10/1974 | Weil et al. | 558/34 |
| 4,395,364 A | 7/1983 | Murata et al. | |
| 4,983,323 A | 1/1991 | Cox et al. | |
| 5,807,816 A * | 9/1998 | Cottrell et al. | 510/235 |
| 6,812,200 B2 * | 11/2004 | Weber et al. | 510/441 |
| 7,467,633 B2 * | 12/2008 | Smith et al. | 134/25.2 |
| 7,642,282 B2 * | 1/2010 | Valenti et al. | 514/438 |
| 7,863,479 B2 * | 1/2011 | Tropsch et al. | 562/36 |
| 7,939,480 B2 * | 5/2011 | Hall et al. | 510/140 |
| 2005/0192190 A1 * | 9/2005 | Hasenzahl et al. | 510/130 |
| 2008/0207939 A1 * | 8/2008 | Tropsch et al. | 558/34 |
| 2008/0261842 A1 * | 10/2008 | Hall et al. | 510/135 |

FOREIGN PATENT DOCUMENTS

| | | |
|---|---|---|
| DE | 4436066 A1 | 4/1996 |
| EP | 0300444 A1 | 1/1989 |
| JP | 55-84399 A | 6/1980 |
| JP | 56-72092 A | 6/1981 |
| JP | 64-47756 A | 2/1989 |
| JP | 0392667 A2 | 10/1990 |
| JP | 2-298598 A | 12/1990 |
| JP | 7-157464 A | 6/1995 |
| JP | 2000-345191 A | 12/2000 |
| JP | 2003-328287 A | 11/2003 |
| JP | 2006-117770 A | 5/2006 |
| WO | WO 2005/077893 * | 8/2005 |

OTHER PUBLICATIONS

International Search Report dated Oct. 7, 2008, for International Application No. PCT/JP2008/062774.
Supplementary European Search Report for corresponding European Patent Application No. 08778191.0, mailed on Mar. 1, 2012.

* cited by examiner

*Primary Examiner* — Mark Eashoo
*Assistant Examiner* — M. Reza Asdjodi
(74) *Attorney, Agent, or Firm* — Birch, Stewart, Kolasch & Birch, LLP

(57) ABSTRACT

The invention relates to a surfactant composition containing an alkyl ether sulfate represented by the following formula (1):

$$RO-(PO)_m(EO)_n SO_3 M \qquad (1)$$

wherein R represents a linear alkyl group having 8 to 24 carbon atoms, PO and EO represent a propyleneoxy group and an ethyleneoxy group, respectively, $\underline{m}$ and $\underline{n}$ denote the average numbers of added moles of PO and EO, respectively, and are numbers meeting: $0 < m < 1$ and $0 < n \leqq 2.3$, respectively, and M represents a cation.

7 Claims, No Drawings

SURFACTANT COMPOSITION

FIELD OF THE INVENTION

The present invention relates to a novel surfactant composition, and, specifically, to a surfactant composition containing an alkyl ether sulfate having a specified structure.

BACKGROUND OF THE INVENTION

As various nonionic surfactants and anionic surfactants which are generally used at present, those derived from alcohols originated from petrochemical raw materials or alcohols originated from oil and fats raw materials are known.

As the method of producing alcohols originated from petrochemical raw materials which alcohols are called synthetic alcohols, for example, there is a method in which a compound having an internal olefin is derived by an oligomerization reaction through ethylene and then converted into an alcohol derivative by oxo reaction. It is known that the synthetic alcohol obtained resultantly is a mixture containing about 20% by weight of branched alcohols besides about 80% by weight of linear alcohols. It is known that various nonionic surfactants and anionic surfactants derived from synthetic alcohols have such excellent characteristics that they are superior in low-temperature stability because they have a lower melting point and low coagulation point than derivatives from linear alcohols.

On the other hand, it is known that various nonionic surfactants and anionic surfactants derived from alcohols originated from oil and fats raw materials which alcohols are one type of natural alcohols have the characteristics such as high foaming ability, low cmc, high cloud point and high emulsifying ability.

As mentioned above, the surfactants derived from synthetic alcohols are different from those derived from natural type alcohols in properties and performances. Therefore, it is usually necessary to use different surfactants according to the use of the surfactant at present.

There is an increased and worldwide demand for natural alcohols in view of the carbon neutral at present. However, surfactants derived from natural alcohols have the drawbacks that they are inferior to those derived from synthetic alcohols in low temperature stability. Therefore, there is a fear that they have not a little adverse influence on the appearance and performance of a system in which they are blended.

If natural alcohols or their derivatives can impart the same characteristics and performances as synthetic alcohols or their derivatives without losing their excellent characteristics and performances, the use of an alcohol in accordance to the state of affairs of raw materials is largely expected regardless of the purpose and use. Therefore, there is currently a strong desire to develop technologies for reforming the properties of natural alcohols and their derivatives.

Examples of major alcohol type anionic surfactants include alkyl sulfates (AS) and alkyl ether sulfates (AES). These surfactants are widely used not only for domestic uses such as dish detergents, shampoos, body detergents, clothing detergents and house detergents but also for chemical uses such as emulsion polymerization emulsifiers and dyeing adjuvants. These surfactants are usually formulated in a concentration as low as about 20% by weight or less in product formulation systems. However, an aqueous AS or AES solution has a low viscosity in this concentration range and it is necessary to adjust the aqueous solution so that the solution has a proper viscosity corresponding to its use (JP-A55-84399, JP-A 56-72092). Accordingly, various thickeners have been investigated so far.

Currently, as the thickeners for various chemical products, fatty acid alkanolamides, such as fatty acid monoethanolamides (JP-A61-114727), fatty acid diglycol amides and fatty acid diethanolamides, reduced irritation to the skin or hairs are preferably used.

SUMMARY OF THE INVENTION

The present invention relates to a surfactant composition comprising an alkyl ether sulfate represented by the following formula (1):

$$RO\text{—}(PO)_m(EO)_nSO_3M \tag{1}$$

wherein R represents a linear alkyl group having 8 to 24 carbon atoms, PO and EO represent a propyleneoxy group and an ethyleneoxy group, respectively, $\underline{m}$ and $\underline{n}$ denote the average numbers of added moles of $\overline{PO}$ and $\overline{EO}$, respectively, and are numbers meeting: $0<m<1$ and $0<n\leqq2.3$, respectively, and M represents a cation.

Also, the present invention relates to a surfactant composition comprising an alkyl ether sulfate represented by the formula (1), produced by steps comprising the following steps (I) to (III):

step (I): a step of adding propylene oxide in an average amount exceeding 0 mol and less than 1 mol to 1 mol of an alcohol having a linear alkyl group having 8 to 24 carbon atoms;

step (II): a step of adding ethylene oxide to the propylene oxide addition product obtained in the step (I) in an average amount exceeding 0 mol and 2.3 mol or less; and step (III): a step of sulfating the alkoxylate obtained in the step (II) and neutralizing the resultant;

$$RO\text{—}(PO)_m(EO)_nSO_3M \tag{1}$$

wherein R represents a linear alkyl group having 8 to 24 carbon atoms, PO and EO represent a propyleneoxy group and an ethyleneoxy group, respectively, $\underline{m}$ and $\underline{n}$ denote the average numbers of added moles of $\overline{PO}$ and $\overline{EO}$, respectively, and are numbers meeting: $0<m<1$ and $0<n\leqq2.3$, respectively, and M represents a cation.

Also, the present invention relates to a surfactant composition which is obtained by blending compounds represented by the following formulae (2) and (3), respectively, in such a condition meeting $0<\alpha<2$ in view of the equation α and comprises an alkyl ether sulfate represented by the formula (1):

$$R^1O\text{-}(EO)_{m'}\text{-}SO_3M \tag{2}$$

$$R^2O\text{-}(AO)_{n'}\text{-}SO_3M \tag{3}$$

wherein $R^1$ and $R^2$, which may be the same as or different from each other, represent a linear alkyl group having 8 to 24 carbon atoms, EO represents an ethyleneoxy group and AO represents an alkyleneoxy group having 3 or 4 carbon atoms, m' denotes the average number of added moles of ethylene oxide and is a number meeting: $0<m'\leqq3$ and n' denotes the average number of added moles of alkylene oxide and is a number meeting: $0<n'\leqq3$ and M represents a cation;

α={(the mole number of the compound (3)×n')/(the mole number of the compound (2)+the mole number of the compound (3)}      Equation (α)

Also, the present invention relates to a detergent composition containing the above surfactant composition of the present invention.

Further, the present invention relates to use of the above surfactant composition of the present invention as a detergent.

Also, the present invention relates to use of the above surfactant composition of the present invention as a thickener and the surfactant composition may be formulated in various products including detergent compositions such as body (including a hair use) detergent compositions, clothing detergent compositions and hard surface detergent compositions and cosmetic compositions.

DETAILED DESCRIPTION OF THE INVENTION

Though fatty acid monoethanolamides and fatty acid diglycol amides are superior in thickening effect, they have the drawbacks that they have a high melting point and are therefore deteriorated in solubility when formulated in detergents or cosmetics. Particularly, when fatty acid monoethanolamides are blended in large amount and stored at low temperature, it is causes of cloudiness and darkness. Therefore, it is limited in amount to be used, product form and applications.

Also, as a method of thickening an aqueous anionic surfactant, there is a method (thickening) in which an inorganic salt such as sodium chloride and sodium sulfate is added to cause coagulation of micells, thereby increasing the concentration of the aqueous solution. These inorganic salts have a higher solubility than the aforementioned thickeners and are therefore used widely and commonly. However, these inorganic salts are reduced in thickening effect corresponding with the amount of these inorganic salts to be added and it is therefore necessary to add these inorganic salts in a large amount when the solution is adjusted to a desired viscosity. However, the addition of a large amount of these inorganic salts gives rise to problems concerning a change in viscosity and irritant feel during washing.

In view of this situation, the inventors of the present invention have started to search an anionic surfactant composition having a high thickening effect, that is, an anionic surfactant producing a high thickening effect even in the case where the concentration of the inorganic salt is low. It is considered that if a surfactant composition having a high thickening effect is obtained in the developments of an alcohol having both the advantageous effects given by an alcohol derived from petrochemical raw materials and an alcohol derived from oil and fats respectively, and also in the developments of various surfactants derived from these alcohols, applications for raw materials of various products including surfactant compositions derived from the alcohol having both the advantageous effects given by an alcohol derived from petrochemical raw materials and an alcohol derived from oil and fats respectively can be expanded.

The inventors of the present invention have made earnest studies and, as a result, found that a surfactant composition containing a specified alkyl ether sulfate produces a high thickening effect and further, the advantageous effects develop advantageous action effects in various products (for example, detergent compositions).

The surfactant composition of the present invention has high sensitivity to inorganic salts and has a high thickening affect. Therefore, even in the case of reducing the amount of an inorganic salt to be added, the surfactant composition can form good thickening system.

<Surfactant Composition>

The surfactant composition of the present invention contains an alkyl ether sulfate represented by the following formula (1).

$$RO-(PO)_m(EO)_n SO_3 M \tag{1}$$

Wherein R represents a linear alkyl group having 8 to 24 carbon atoms, PO and EO represent a propyleneoxy group and an ethyleneoxy group, respectively, and $\overline{m}$ and $\overline{n}$ denote the average numbers of added moles of PO and EO, respectively, and are numbers meeting: $0<\overline{m}<1$ and $0<\overline{n}\leqq 2.3$, respectively, and M represents a cation.

Here, the alkyl group of R in the formula (1) has preferably 8 to 18, more preferably 10 to 16 and even more preferably 12 to 14 carbon atoms from the viewpoint of the availability and handling ability of raw materials.

Also, $\overline{m}$ in the formula (1) is the average number of added moles of PO and is a number exceeding 0 and less than 1. $\overline{m}$ is preferably 0.1 to 0.9 and more preferably 0.2 to 0.7 from the viewpoint of reactivity and thickening performance in the production.

Also, $\overline{n}$ in the formula (1) is the average number of added moles of EO and is a number exceeding 0 and 2.3 or less. $\overline{n}$ is preferably 0.5 to 2.0 and more preferably 1.0 to 2.0 from the viewpoint of convenience in controlling thickening effect.

In overall consideration of reactivity, thickening performance and convenience in controlling thickening effect in the production, the average numbers of added moles of PO and EO are as follows: preferably 0.1 to 0.9 of PO and 0.5 to 2.0 of EO, more preferably 0.2 to 0.7 of PO and 1.0 to 2.0 of EO, even more preferably 0.4 to 0.7 of PO and 1.0 to 1.5 of EO.

Also, M in the formula (1) is a cationic group forming a salt. Examples of M include alkali metal ions, alkali earth metal ions, ammonium ions and alkanol ammonium ions such as triethanol ammonium ions. Examples of the alkali metal include sodium, potassium and lithium and examples of the alkali earth metals include calcium. Among these compounds, sodium and potassium are more preferable and sodium is even more preferable.

The surfactant composition of the present invention is produced and used in the form of an aqueous solution or a hydrate paste from the viewpoint of handling ability. However, the surfactant composition of the present invention may be one constituted of an alkyl ether sulfate represented by the formula (1). Also, the surfactant composition of the present invention may be one constituted of an alkyl ether sulfate represented by the formula (1) and water.

The alkyl ether sulfate represented by the formula (1) which sulfate is used in the surfactant composition of the present invention may be produced, for example, by a process containing the following steps (I) to (III), though there is no particular limitation to it.

Step (I): a step of adding propylene oxide in an average amount exceeding 0 mol and less than 1 mol to 1 mol of an alcohol having a linear alkyl group having 8 to 24 carbon atoms.

Step (II): a step of adding ethylene oxide to the propylene oxide addition product obtained in the above step (I) in an average amount exceeding 0 mol and 2.3 mol or less.

Step (III): a step of sulfating the alkoxylate obtained in the above step (II), followed by neutralizing.

Also, the method used to obtain a surfactant composition having the same effect as the surfactant composition of the present invention include a method in which compounds represented by the following formulae (2) and (3), respectively, are blended in such a condition meeting $0<\alpha<2$ in view of the equation α, besides the method involving the above steps (I) to (III):

$$R^1O\text{-}(EO)_{m'} \cdot SO_3 M \tag{2}$$

$$R^2O\text{-}(AO)_{n'} \cdot SO_3 M \tag{3}$$

Where in $R^1$ and $R^2$, which may be the same as or different from each other, represent a linear alkyl group having 8 to 24 carbon atoms, EO represents an ethyleneoxy group and AO represents an alkyleneoxy group having 3 to 4 carbon atoms, respectively, m' denotes the average number of added moles of ethylene oxide and is a number meeting: $0<m'\leq 3$, n' denotes the average number of added moles of alkylene oxide and is a number meeting: $0<n'\leq 3$ and M represents a cation.

$\alpha = \{(\text{Molar number of the compound }(3) \times n')/(\text{Molar number of the compound }(2) + \text{Molar number of the compound }(3))\}$   Equation ($\alpha$)

It is more preferable to blend them in such a condition meeting $0<\alpha<1$.

The method of mixing the compounds represented by the formulae (2) and (3) with each other is not limited to the aforementioned method. No limitation on how to mix these compounds is made and any mixing method is acceptable insofar as the two components, the compound represented by the formula (2) and the compound represented by the formula (3), meet the equation ($\alpha$). For example, it is applicable to contain a third component other than the compounds represented by the formulae (2) and (3). It is also applicable to mix one of the compound represented by the formula (3) and the compound represented by the formula (2) with a mixture of a third component and the other compound.

The surfactant composition of the present invention and particularly, the composition containing an alkyl ether sulfate obtained by a process involving the steps (I) to (III) according to the present invention may be a mixture of compounds represented by the following formulae (4) to (7) and such a mixture is regarded as the alkyl ether sulfate (single material) that meets the equation (1).

$\text{RO—SO}_3\text{M}$   (4)

$\text{RO—(PO)}_x\text{SO}_3\text{M}$   (5)

$\text{RO-(EO)}_y\text{SO}_3\text{M}$   (6)

$\text{RO—(PO)}_z(\text{EO})_{z'}\text{SO}_3\text{M}$   (7)

The ratio of the compound represented by the formula (4) in the surfactant composition of the present invention is preferably 8 to 82 mol %, more preferably 8 to 31 mol % and even more preferably 12 to 31 mol % in the sum of the compounds represented by the formulae (4) to (7).

The ratio of the compound represented by the formula (5) in the surfactant composition of the present invention is preferably 10 to 69 mol %, more preferably 10 to 36 mol % and even more preferably 11 to 29 mol % in the sum of the compounds represented by the formulae (4) to (7).

The ratio of the sum of the compounds represented by the formulae (6) and (7) in the surfactant composition of the present invention is preferably 17 to 67 mol %, more preferably 45 to 65 mol % and even more preferably 45 to 60 mol in the sum of the compounds represented by the formulae (4) to (7).

x, y, z and z' in the formulae (4) to (7) are respectively an integer of 1 or more and R and M accord to those explained in the formula (1).

The step (I) is a step of adding propylene oxide in an average amount exceeding 0 mol and less than 1 mol to an alcohol having a linear alkyl group having 8 to 24 carbon atoms.

The alkyl group of the alcohol to be used in the present invention is a linear alkyl group having 8 to 24 carbon atoms. The alkyl group has preferably 8 to 18 carbon atoms, more preferably 10 to 16 carbon atoms and even more preferably 12 to 14 carbon atoms from the viewpoint of the availability and handling ability of raw materials.

Also, the amount of propylene oxide to be used based on one mol of the above alcohol is preferably an amount enough to produce the alkyl ether sulfate represented by the formula (I). Specifically, though the amount of propylene oxide exceeds 0 mol and is less than 1 mol based on 1 mol of the above alcohol, it is preferably 0.1 to 0.9 mol and more preferably 0.2 to 0.7 mol from the viewpoint of reactivity of the production and thickening performance.

The step (II) is a step of adding ethylene oxide in an average amount exceeding 0 mol and 2.3 mol or less to the propylene oxide addition product obtained in the above step (I). The amount of ethylene oxide to be used based on 1 mol of the above alcohol is preferably an amount enough to produce the alkyl ether sulfate represented by the formula (4). Specifically, though the average amount of ethylene oxide exceeds 0 mol and is 2.3 mol or less based on 1 mol of the above alcohol, it is preferably 0.5 to 2.0 mol and more preferably 1.0 to 2.0 mol from the viewpoint of convenience in controlling thickening effect.

As the method of carrying out the steps (I) and (II), conventionally known methods may be used. Specifically, an autoclave is charged with an alcohol and, for example, KOH as a catalyst in an amount of 0.5 to 1 mol % based on the alcohol, and the alcohol is heated and dehydrated to allow specified amounts of propylene oxide and ethylene oxide to undergo an addition reaction at a temperature of 130 to 160° C., whereby the alkyl ether sulfate can be produced. At this time, the form of addition is block addition, and the process is carried out in the order of the addition of propylene (step (I)) and the addition of ethylene oxide (step (II)). The autoclave to be used is desirably equipped with a stirrer, a temperature control device and an automatic feeder.

The step (III) is a step of sulfating the alkoxylate obtained in the above step (II), followed by neutralizing. Examples of the sulfating method include methods using sulfur trioxide (liquid or gas), sulfur trioxide-containing gas, fuming sulfuric acid or chlorosulfonic acid. In particular, a method in which sulfur trioxide is continuously supplied together with the alkoxylate in a gas or liquid state is preferable from the viewpoint of preventing the generation of waste sulfuric acid and waste hydrochloric acid.

Example of a method of neutralizing the sulfate include a batch system in which the sulfate is added to a specified amount of a neutralizing agent with stirring to neutralize and a continuous system in which the sulfate and a neutralizing agent are continuously supplied to the inside of a pipe to neutralize using a stirring mixer, though there is no limitation to the neutralization method in the present invention. Examples of the neutralizing agent used here include an aqueous alkali metal solution, aqueous ammonia and triethanolamine. An aqueous alkali metal solution is preferable and sodium hydroxide is more preferable.

The surfactant composition of the present invention is produced and used in the form of an aqueous solution and a hydrate paste from the viewpoint of handling ability and transportational advantage, though no particular limitation is imposed on it. The amount of the surfactant (amount of the alkyl ether sulfate represented by the formula (1)) in the surfactant composition of the present invention is preferably 5 to 85% by weight, more preferably 10 to 80% by weight and even more preferably 20 to 80% by weight, and even more preferably 60 to 80% by weight from the viewpoint of transportational and formulating advantages.

As an example of the surfactant composition of the present invention, a composition containing an alkyl ether sulfate obtained by sulfating/neutralizing an alkoxylate obtained by adding propylene oxide in an average amount of 0.2 to 0.8 mol and ethylene oxide in an average amount of 0.5 to 2 mol to 1 mol of a mixture alcohol (12 carbon atoms/14 carbon atoms) ensures to obtain a high thickening effect even in the case where the concentration of the inorganic salt is low.

Also, a high thickening effect can also be obtained by adding the compound represented by the formula (3) to an aqueous solution containing the inorganic salt and the anionic surfactant (particularly, a compound represented by the formula (2)).

<Detergent Composition>

The surfactant composition of the present invention has the characteristic that it is superior in thickening effect. Therefore, the surfactant composition of the present invention may be compounded in various products such as detergent compositions and cosmetic compositions corresponding to the use and object of each product. The surfactant composition of the present invention is particularly effective for detergent compositions which need a thickening effect. Examples of the detergent composition include body (including a hair use) detergent compositions, clothing detergent compositions and hard surface detergent compositions.

The content of the surfactant composition of the present invention is preferably 0.5 to 27% by weight, more preferably 1 to 25% by weight, even more preferably 5 to 25% by weight and even more preferably 5 to 20% by weight in the detergent composition, though no particular limitation is imposed on it.

Besides the surfactant composition of the present invention, various additives which are usually used in the fields concerned may be optionally blended corresponding to the object, these additives including surfactants (other anionic surfactants, nonionic surfactants, amphoteric surfactants and cationic surfactants): viscosity regulating agents; foaming agents; higher alcohols and higher fatty acids; various cationic, anionic or nonionic polymers; silicones; polyols; pearling agents; alkali agents; sequestering agents; antiseptics; perfumes; dyes; and inorganic salts. The inorganic salt is preferably one or more types of inorganic salts selected from alkali metal salts of hydrochloric acid, hydrobromic acid, sulfuric acid, nitric acid, carbonic acid or phosphoric acid. Among these metal salts, alkali metal salts of hydrochloric acid, for example, sodium chloride are more preferable. Also, the content of the inorganic salt is preferably 1 to 3% by weight in the detergent composition.

The surfactant composition may contain an inorganic salt (component (B)). Specifically, the present invention provides a surfactant composition which contains (A) 5 to 27% by weight of an alkyl ether sulfate represented by the above formula (1), (B) 1 to 3% by weight of one or more inorganic salts selected from alkali metal salts of hydrochloric acid, hydrobromic acid, sulfuric acid, nitric acid, carbonic acid, phosphoric acid or the like and (C) water and has a viscosity of 100 to 10000 mPa·s at 30° C. This viscosity is measured in the condition of examples which will be explained later.

As the inorganic salt which is the component (B) in the surfactant composition of the above detergent composition, sodium chloride, potassium chloride, sodium bromide, sodium sulfate, sodium nitrate, sodium carbonate, monohydrogen sodium phosphate and dihydrogen sodium phosphate are exemplified. Among these compounds, sodium chloride, potassium chloride, sodium sulfate and sodium carbonate are preferable and sodium chloride and sodium sulfate are more preferable.

EXAMPLES

The following examples explain the embodiments of the present invention. These embodiments explain examples of the present invention. However, these examples are not intended to be limiting of the present invention.

Example 1

An autoclave equipped with a stirrer, a temperature-control device and an automatic feeder was charged with 3447 g of an alcohol having 12 carbon atoms (trade name: Kalcol 2098, manufactured by Kao Corporation), 1341 g of an alcohol having 14 carbon atoms (trade name: Kalcol 4098, manufactured by Kao Corporation) and 6.8 g of KOH, which was then dehydrated at 110° C. under a pressure of 1.3 kPa for 30 minutes. After the alcohol was dehydrated, the atmosphere in the autoclave was replaced with nitrogen. After the alcohol was heated to 120° C., 575 g of PO was charged in the autoclave. The mixture was subjected to an addition reaction and aging carried out at 120° C. and then, the mixture was heated to 145° C. and 1625 g of EO was charged in the autoclave. The mixture was subjected to an addition reaction and aging carried out at 145° C. and then cooled to 80° C. and unreacted EO was removed under a pressure of 4.0 kPa. After the unreacted EO was removed, 7.3 g of acetic acid was added in the autoclave and the resulting mixture was stirred at 80° C. for 30 minutes. Then, the mixture was discharged to obtain an alkoxylate in which the average number of added moles of PO was 0.4 mol and the average number of added moles of EO was 1.5 mol.

The obtained alkoxylate was sulfated using $SO_3$ gas in a falling film reactor (hereinafter referred to as FFR). The obtained sulfate was neutralized by an aqueous NaOH solution to obtain a composition containing an alkyl ether sulfate. NaCl and ion exchanged water were added to the alkyl ether sulfate composition to prepare an evaluation sample containing a surfactant in a concentration of 20% by weight. The evaluation sample is constituted of a surfactant effective content, NaCl and water, wherein various concentrations shown in Table 1 were used as the concentration of NaCl. The viscosity of the obtained evaluation sample was measured by a Brookfield-type viscometer (B-type viscometer). The conditions of measurement are shown below. The composition of the evaluation sample (concentrations of the surfactant and NaCl) and the results of the measurement of viscosity are shown in Table 1. In Table 1, EOp is the average number of added moles of ethylene oxide and POp is the average number of added moles of propylene oxide.

(Measurement Conditions)
  Measuring instrument of viscosity: Brookfield-type viscometer (trade name: "DVL-BII", manufactured by TOKIMEC Inc.)
  Sample temperature: 30° C.
  Measuring time: 90 seconds
  Rotor No.: 1 to 4
  Rotation: 30 rpm Example 2

An alkyl ether sulfate composition in which the average number of added moles of PO was 0.4 mol and the average number of added moles of EO was 2.0 mol was obtained in the same method as in Example 1. The obtained alkyl ether sulfate composition was used to prepare an evaluation sample in the same manner as in Example 1 to measure the viscosity of the sample. The composition of the evaluation sample and the results of measurement of viscosity are shown in Table 1.

Example 3

An alkyl ether sulfate composition in which the average number of added moles of PO was 0.7 mol and the average number of added moles of EO was 2.0 mol was obtained in the same method as in Example 1. The obtained alkyl ether sulfate composition was used to prepare an evaluation sample in the same manner as in Example 1 to measure the viscosity of the sample. The composition of the evaluation sample and the results of measurement of viscosity are shown in Table 1.

Comparative Example 1

An alkyl ether sulfate (trade name: Emal 270J) manufactured by Kao Corporation was used to prepare an evaluation sample in the same method as in Example 3 and the viscosity of an aqueous solution of the sample was measured. The composition of the evaluation sample and the results of measurement of viscosity are shown in Table 1.

Comparative Example 2

An alkyl ether sulfate composition in which the average number of added moles of PO was 1.0 mol and the average number of added moles of EO was 2.0 mol was obtained in the same method as in Example 1. The obtained alkyl ether sulfate composition was used to prepare an evaluation sample in the same manner as in Example 1 to measure the viscosity of the sample. The composition of the evaluation sample and the results of measurement of viscosity are shown in Table 1.

Comparative Example 3

An alkyl ether sulfate composition in which the average number of added moles of PO was 0.5 mol and the average number of added moles of EO was 2.5 mol was obtained in the same method as in Example 1. The obtained alkyl ether sulfate composition was used to prepare an evaluation sample in the same manner as in Example 1 to measure the viscosity of the sample. The composition of the evaluation sample and the results of measurement of viscosity are shown in Table 1.

Comparative Example 4

An alkyl ether sulfate composition in which the average number of added moles of PO was 0.5 mol and the average number of added moles of EO was 2.5 mol was obtained using a mixture alcohol (12 carbon atoms and 13 carbon atoms) (trade name: NEODOL23, manufactured by Shell Co., Ltd.) having a blanched alkyl group in the same method as in Example 1. The obtained alkyl ether sulfate composition was used to prepare an evaluation sample in the same manner as in Example 1 to measure the viscosity of the sample. The composition of the evaluation sample and the results of measurement of viscosity are shown in Table 1.

TABLE 1

|  |  |  | Example | | | Comparative example | | | |
|---|---|---|---|---|---|---|---|---|---|
|  |  |  | 1 | 2 | 3 | 1 | 2 | 3 | 4 |
| Alkyl group |  |  |  | C12/C14 linear | |  | C12/C14 linear | | C12/C13 branched |
| the number of added moles of PO · EO |  |  | PO: 0.4 mol EO: 1.5 mol | PO: 0.4 mol EO: 2.0 mol | PO: 0.7 mol EO: 2.0 mol | PO: 0 mol EO: 2.0 mol | PO 1.0 mol EO: 2.0 mol | PO: 0.5 mol EO: 2.5 mol | PO: 0.5 mol EO: 2.5 mol |
| Concentration of surfactant (% by mass) |  |  | 20 | 20 | 20 | 20 | 20 | 20 | 20 |
| Viscosity (mPa · s) | Concentration of NaCl (% by mass) | 0 | 8 | 9 | 7 | 9 | 8 | 8 | 6 |
|  |  | 1 | 48 | 22 | 15 | 23 | 10 | 7 | 4 |
|  |  | 1.5 | 717 | 160 | 146 | 41 | 51 | 14 | 57 |
|  |  | 2 | 7730 | 1446 | 1337 | 343 | 416 | 52 | 360 |

As is clear from the table, the surfactant composition containing the alkyl ether sulfate of the example produced a higher thickening effect than the surfactant composition containing the alkyl ether sulfate of the comparative example. Also, the thickening effect is significantly large in the range of POp and EOp according to the present invention.

Example 4 and Comparative Example 5

A sodium alkyl (12 carbon atoms/14 carbon atoms: 75% by weight/25% by weight) ether sulfate (surfactant (1-1)) in which the average number of added moles of EO was 2 mol was blended with a sodium alkyl (12 carbon atoms/14 carbon atoms: 72% by weight/28% by weight) ether sulfate (surfactant (2-1)) in which the average number of added moles of PO was 1 mol in the ratios as shown in Table 1. Further, sodium chloride and ion exchange water were added to the mixture to prepare an evaluation sample in which the concentration of all surfactants was 20% by weight and the concentration of sodium chloride was 1.5% by weight. The viscosity of the obtained evaluation sample was measured in the same method as in Examples 1 to 3. The composition of the evaluation sample and the results of measurement of viscosity are shown in Table 2.

TABLE 2

|  | Example | | | | Comparative example |
| --- | --- | --- | --- | --- | --- |
|  | 4-1 | 4-2 | 4-3 | 4-4 | 5-1 |
| Surfactant(1-1) [formula(2), the average number of added moles of EO: 2] | 16 g | 12 g | 8 g | 4 g | 20 g |
| Surfactant(2-1) (formula(3), the average number of added moles of PO: 1] | 4 g | 8 g | 12 g | 16 g | 0 g |
| Sodium chloride | 1.5 g | 1.5 g | 1.5 g | 1.5 g | 1.5 g |
| Ion-exchanged water | 78.5 g | 78.5 g | 78.5 g | 78.5 g | 78.5 g |
| Value of formula (α) | 0.2 | 0.4 | 0.6 | 0.8 | 0 |
| Viscosity(mPa · s) | 104 | 396 | 986 | 1839 | 32 |

As is clear from Table 2, the viscosity of an aqueous anionic surfactant solution decreased in thickening effect can be increased by adding the compound represented by the above formula (3) and also, the thickening behavior of the aqueous solution can be controlled by changing the amount of the compound represented by the above formula (3).

The invention claimed is:

1. A surfactant composition comprising an alkyl ether sulfate represented by the following formula (1):

$$RO-(PO)_m(EO)_nSO_3M \quad (1)$$

wherein R represents a linear alkyl group having 8 to 24 carbon atoms, PO and EO represent a propyleneoxy group and an ethyleneoxy group, respectively, m and n denote the average numbers of added moles of PO and EO, respectively, and are numbers meeting: $0.1 \leq m \leq 0.7$ and $0 < n \leq 2.3$, respectively, and M represents a cation.

2. A surfactant composition according to claim 1, comprising an alkyl ether sulfate represented by the formula (1), produced by steps comprising the following steps (I) to (III):

step (I): a step of adding propylene oxide in an average amount exceeding 0 mol and less than 1 mol to 1 mol of an alcohol having a linear alkyl group having 8 to 24 carbon atoms;

step (II): a step of adding ethylene oxide to the propylene oxide addition product obtained in the step (I) in an average amount exceeding 0 mol and 2.3 mol or less; and step (III): a step of sulfating the alkoxylate obtained in the step (II) and neutralizing the resultant.

3. A surfactant composition according to claim 1, which is obtained by blending compounds represented by the following formulae (2) and (3), respectively, in such a condition meeting $0 < \alpha < 2$ in view of the Equation (α) and comprises an alkyl ether sulfate represented by the formula (1):

$$R^1O-(EO)_{m'}SO_3M \quad (2)$$

$$R^2O-(AO)_{n'}SO_3M \quad (3)$$

wherein $R^1$ and $R^2$, which may be the same as or different from each other, represent a linear alkyl group having 8 to 24 carbon atoms, EO represents an ethyleneoxy group and AO represents an alkyleneoxy group having 3 or 4 carbon atoms, m' denotes the average number of added moles of ethylene oxide and is a number meeting: $0 < m' \leq 3$ and n' denotes the average number of added moles of alkylene oxide and is a number meeting: $0 < n' \leq 3$ and M represents a cation;

$$\alpha = \{(\text{the mole number of the compound } (3) \times n')/(\text{the mole number of the compound } (2) + \text{the mole number of the compound } (3))\} \quad \text{Equation } (\alpha).$$

4. A detergent composition comprising the surfactant composition as claimed in any one of claims 1 to 3.

5. A surfactant composition according to claim 1 or 2, wherein $0.2 \leq m \leq 0.7$.

6. A surfactant composition according to claim 1, wherein the average numbers of added moles of PO and EO are 0.2 to 0.7 of PO and 0.5 to 2.0 of EO.

7. A surfactant composition according to claim 1, wherein the average numbers of added moles of PO and EO are 0.2 to 0.7 of PO and 1.0 to 2.0 of EO.

* * * * *